United States Patent [19]

Bird

[11] 4,060,078
[45] Nov. 29, 1977

[54] VENTILATOR AND METHOD

[76] Inventor: Forrest M. Bird, 212 NW. Cerritos, Palm Springs, Calif. 92262

[21] Appl. No.: 605,529

[22] Filed: Aug. 18, 1975

[51] Int. Cl.² ............................................. A61M 16/00
[52] U.S. Cl. ............................. 128/145.8; 137/624.14
[58] Field of Search ............... 128/145.8, 145.6, 145.5, 128/142.2, 142.3, 146.5, 188, DIG. 17; 137/624.13, 624.14

[56] References Cited

U.S. PATENT DOCUMENTS

| | | | |
|---|---|---|---|
| 3,068,856 | 12/1962 | Bird et al. | 128/145.5 |
| 3,138,152 | 6/1964 | Wilson | 128/145.8 |
| 3,234,932 | 2/1966 | Bird et al. | 128/145.6 |
| 3,384,105 | 5/1968 | Leggett | 137/624.14 |
| 3,406,682 | 10/1968 | Engstrom | 128/145.8 |
| 3,434,471 | 3/1969 | Liston | 128/145.8 |
| 3,662,751 | 5/1972 | Barkalow et al. | 128/145.8 |
| 3,840,006 | 10/1974 | Buck et al. | 128/145.8 |
| 3,903,881 | 9/1975 | Weigl | 128/145.6 |
| 3,905,362 | 9/1975 | Eyrick et al. | 128/145.8 |
| 3,915,164 | 10/1975 | Bird | 128/145.8 |
| 3,916,889 | 11/1975 | Russell | 128/145.8 |

*Primary Examiner*—Dalton L. Truluck
*Assistant Examiner*—Henry J. Recla

*Attorney, Agent, or Firm*—Flehr, Hohbach, Test, Albritton & Herbert

[57] ABSTRACT

Ventilator having an inhalation phase and an exhalation phase in its operative cycle for use with a source of gas under pressure. A demand flow accelerator is responsive to the pressure of the gases in a breathing head assembly and provides additional gases to the breathing head assembly when the pressure of the gases in the breathing head assembly falls below a predetermined pressure. A sensor is also provided responsive to the pressure of the gases in the breathing head assembly for supplying gases to the breathing head assembly when the pressure of the gases in the breathing head assembly falls below a predetermined value to cause the patient to exhale against a substantially constant positive airway pressure. An additional sensor is also provided which is sensitive to the airway pressure being sensed for bleeding gases from the breathing circuit when pressure greater than a predetermined pressure are reached. Lock-out means is provided for locking out an inspiratory phase which exceeds a predetermined time. Starting means is provided for ensuring that the ventilator will be switched to an expiratory phase before an inspiratory phase is initiated.

33 Claims, 5 Drawing Figures

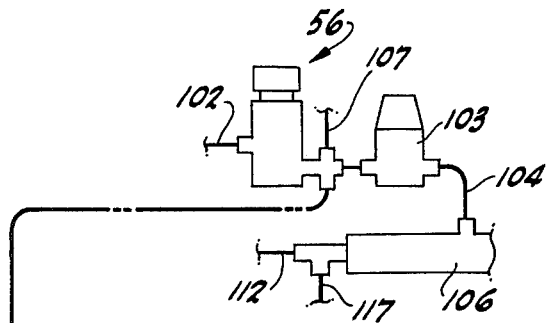
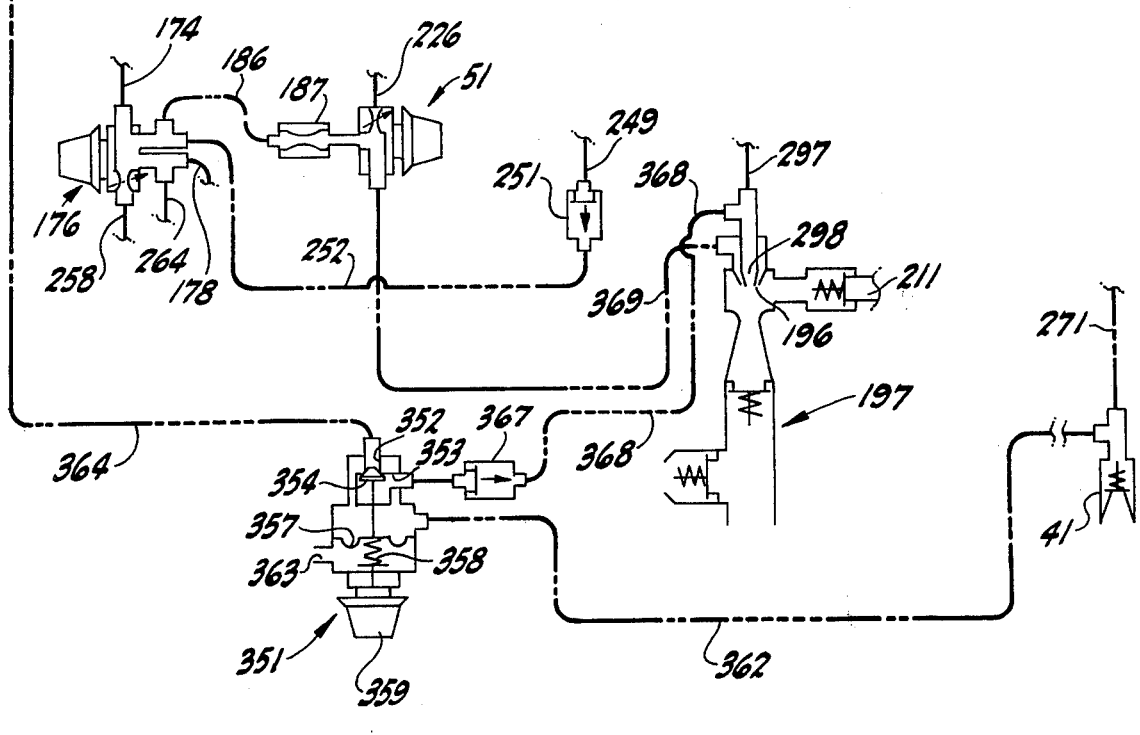
FIG-4

VENTILATOR AND METHOD

BACKGROUND OF THE INVENTION

In U.S. Pat. No. 3,842,828 there is disclosed a ventilator which utilizes an intermittent mandatory ventilation (hereinafter IMV) concept which has been found to be very successful when applied to babies. However, in the IMV concept utilized in that ventilator, a constant flow is provided into the breathing circuit. In order to accommodate adults with a similar concept, much larger flows are required which, in view of the high cost of gases, would be almost prohibitive to utilize. There is, therefore a need for a new and improved ventilator having IMV capabilities which can be utilized in conjunction with adults as well as infants.

SUMMARY OF THE INVENTION AND OBJECTS

The ventilator and method of the present invention utilize time cycling for the inspiratory and expiratory phases. Demand flow accelerator means is provided which is responsive to the spontaneous breathing of the patient for supplying additional inspiratory gases to the patient upon demand. Automatic baseline compensation means is provided for supplying gases to the exhalation valve of the patient so that the patient must exhale against a constant positive airway pressure. The flow from the automatic baseline compensator means is increased and decreased in response to the pressure being sensed in the breathing head. Inspiratory compliance compensations means is provided for bleeding off gases to ambient from the gases being supplied to the breathing head in response to pressures being sensed in the breathing head.

In general, it is an object of the present invention to provide a ventilator and method which is time cycled between the inspiratory and expiratory phases and in which an inspiratory phase can be initiated upon the demand of the patient.

Another object of the invention is to provide a ventilator and method of the above character in which intermittent mandatory ventilation can be provided with interruptable flow to the patient.

Another object of the invention is to provide a ventilator and method of the above character in which automatic baseline compensation means is provided to ensure that the patient must exhale against a substantially constant positive airway pressure.

Another object of the invention is to provide a ventilator and method of the above character in which the automatic baseline compensation means is responsive to the pressure of the gases in the breathing circuit.

Another object of the invention is to provide a ventilator and method of the above character in which an inspiratory phase can be manually initiated.

Another object of the invention is to provide a ventilator and method of the above character in which inspiratory compliance compensation means is provided to bleed off gases from the breathing circuit near the end of the inspiratory phase so that the pressure in the breathing circuit will not substantially exceed a predetermined value.

Another object of the invention is to provide a ventilator and method of the above character in which the inspiratory compliance compensation means provides a variable flow depending upon the pressure being sensed in the breathing circuit.

Another object of the invention is to provide a ventilator and method of the above character which will lock out the inspiratory phase after a predetermined period of time and permit the patient to freely exhale.

Another object of the invention is to provide a ventilator and method of the above character in which the inspiratory time and the expiratory time are independent of each other.

Another object of the invention is to provide a ventilator and method of the above character in which the intermittent mandatory ventilation is time cycled.

Another object of the invention is to provide a ventilator and method of the above character in which the timing between intermittent mandatory ventilation can be adjusted.

Another object of the invention is to provide a ventilator and method of the above character in which the pressure in the proximal airway is sensed.

Another object of the invention is to provide a ventilator and method of the above character in which inspiratory flow deceleration can be provided.

Another object of the invention is to provide a ventilator and method of the above character in which demand flow acceleration can be provided.

Another object of the invention is to provide a ventilator and method of the above character which maintains a more constant tidal volume as pulmonary resistances increase.

Additional objects and features of the invention will appear from the following description in which the preferred embodiment is set forth in detail in conjunction with the accompanying drawings.

BRIEF DESCRIPTION OF THE DRAWINGS

FIG. 1A is a cross sectional view of a portion of the breathing head shown in FIG. 1.

FIG. 4 is a partial flow diagram, partially in schematic form, of another embodiment of the ventilator of the present invention.

DESCRIPTION OF PREFERRED EMBODIMENT

Figure 1:
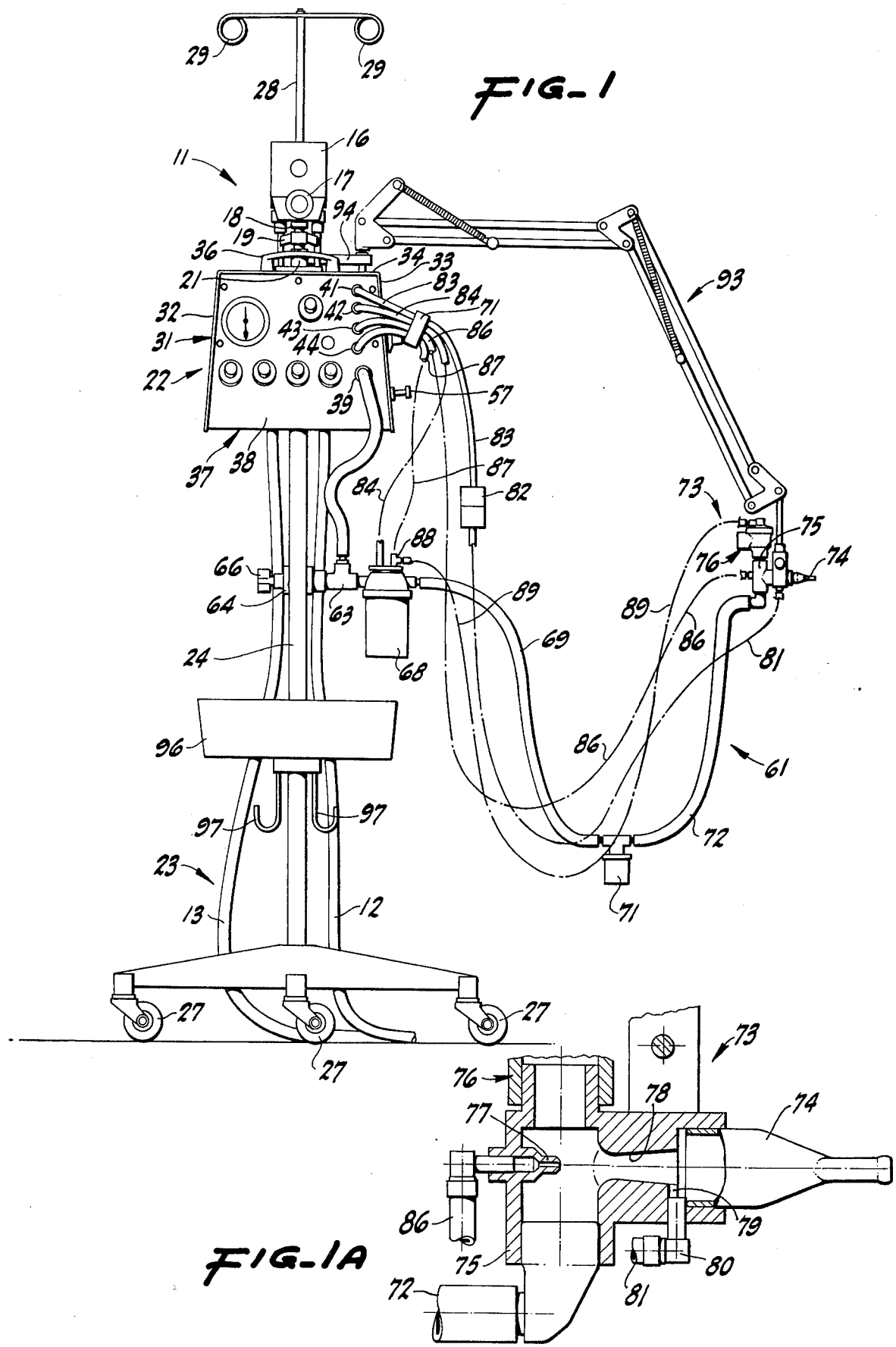
FIG. 1 is a front elevational view of a ventilator incorporating the present invention.
Figure 2:
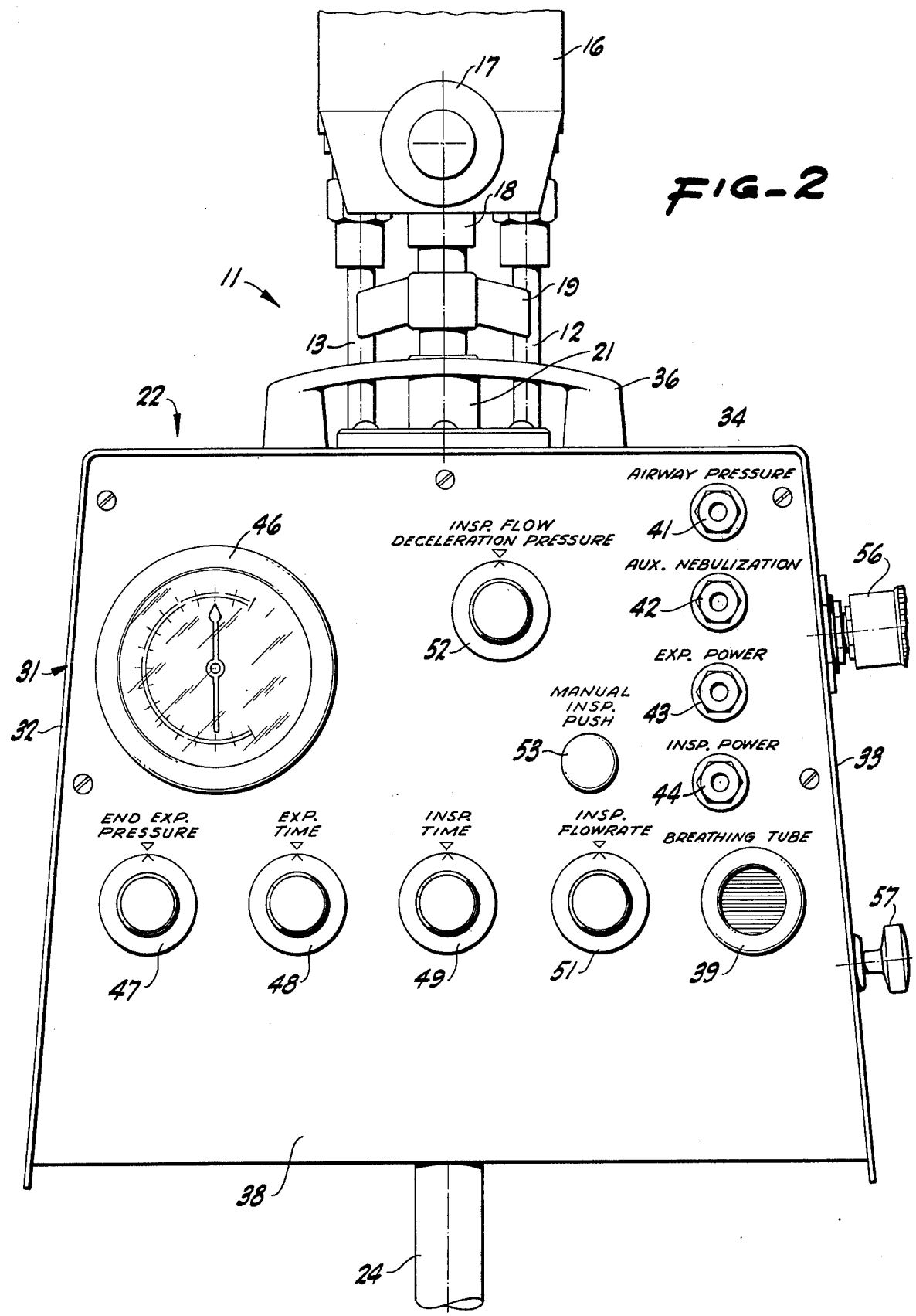
FIG. 2 is an enlarged front elevational view of the portion of the ventilator shown in FIG. 1.

The ventilator which is shown in FIG. 1 of the drawings is adapted to be connected to a source of gas under a suitable pressure as, for example, 50 psi. For this purpose, the ventilator has been provided with tubes 12 and 13 which can be connected to suitable gas sources such as an oxygen supply and an air supply (not shown) such as conventionally provided in a hospital. The tubes 12 and 13 are connected to a blender 16 of the type described in U.S. Pat. No. 3,737,627. The blender is provided with a control knob 17 for adjusting the ratio of the gases supplied to the outlet 18 of the blender which is connected by a fitting 19 to the inlet 21 mounted on the ventilator case 22. The case 22 is carried by a support stand 23 which is provided with an upright support member 24. The support member 24 is carried by a four-legged base 26 which has casters 27 mounted on the outer extremities thereof. A support rod 28 is slidably mounted in the support member 24 and has mounted thereon wire loops 29 which can be utilized for supporting equipment utilized in conjunction with the ventilator 11.

The case 22 is provided with a U-shaped member 31 which forms side walls 32 and 33 and a top wall 34. A handle 36 is provided on the top wall for carrying the ventilator case 22. Another U-shaped member 37 is mounted within the U-shaped member 31 and forms a front panel 38.

The front panel is provided with a breathing tube outlet or receptacle 39 and four smaller outlets 41, 42, 43 and 44 which can be identified respectively as an airway pressure outlet 41, auxiliary nebulization outlet 42, expiratory power outlet 43, and inspiratory power outlet 44. A manometer 46 is also mounted in the front panel 38. In addition, there are provided a plurality of controls on the front panel which include an expiratory pressure control valve assembly 47, an expiratory time control valve assembly 48, an inspiratory time control valve assembly 49, an inspiratory flow rate control valve assembly 51, and an inspiratory flow deceleration pressure control valve assembly 52. A manual inspiration pushbutton assembly 53 is also mounted on the front panel. The main on/off control valve assembly 56 is mounted on the side wall 33. A hanger or support rod assembly 57 is also mounted in the side wall 33.

A breathing head assembly 61 forms a part of the ventilator and is in communication with the breathing tube receptacle 39 and the outlets 41–44. The breathing head assembly 61 includes a large tube 62 which has one end mounted in the breathing tube receptacle 39. The other end of the tube 62 is connected to a tee 63 which is carried by a U-shaped clamp 64. The U-shaped clamp 64 is positioned on the support member 24 and is frictionally retained thereon by rotation of a knob 66 to frictionally secure the clamp 64 to the support member 24. One end of a 500 cc nebulizer 68 of the type described in U.S. Pat. No. 3,172,406 is mounted in one end of the tee 63 so that the gases passing through the large tube 62 pass through the main flow passage in the nebulizer 68 where they are supplied to one end of another large tube 69. The other end of the tube 69 is connected to one end of a water trap assembly 71 of a type described in copending application Ser. No. 534,852, filed Dec. 20, 1974. Another tube 72 is connected to the other end of the water trap assembly 71 and connects the same to a breathing head 73 which has a patient adapter 74 mounted therein. The breathing head 74 includes a tee-shaped venturi member 75 which has the patient adapter 74 mounted in one leg. A conventional exhalation assembly 76 is mounted in another leg and the large tube 72 is connected to the remaining leg of the member 75 and is adapted to direct a jet of gases through a venturi-like passageway 78 provided in the member and into the patient adapter 74. A venturi sensing port 79 is positioned in the member 75 in a position to sense the pressure in the patient airway. As hereinafter described, the sensitivity of the measurement can be adjusted by different positions for the port 79 relative to the passageway 78.

A fitting 80 is mounted in the port 79. A tube 81 is connected to the fitting 80 into the breathing head 73 and is also connected to one end of a reservoir 82. The other end of the reservoir 82 is connected by a tube 83 to the airway pressure fitting 41 provided on the front panel 38. A tube 84 is connected to the auxiliary nebulization fitting 42 provided on the front panel 38 and is connected to one of the jets of the 500 cc nebulizer 68. The expiratory power fitting or outlet 43 is connected by a tube 86 to the nozzle 77. The inspiratory power fitting or outlet 44 is connected by a tube 87 to a tee 88 which is mounted in the other of the jets of the 500 cc neublizer 68. Another leg of the tee 88 is connected by a tube 89 to the exhalation valve assembly 76. A clamp 91 is provided for holding the tubes 83, 84, 86 and 87 is a prearranged order so that when they are disconnected from the sockets or outlets 41, 42, 43 and 44 they will remain in the proper relationship.

As shown in the drawings, a parallogram type support arm assembly 93 is provided for supporting the outer extremity of the breathing head assembly 61. The support arm assembly 93 is carried by bar 94 which is secured to the support member 24. A tray 96 is mounted upon the support member 24 and is provided therebelow with a pair of hooks 97.

Mounted within the case 22 there are provided a number of additional parts and components which form a part of the ventilator 11. Since these parts and components are substantially conventional, they will not be described in detail but will only be discussed in connection with the functions which they perform in the ventilator as hereinafter described.

Figure 3:
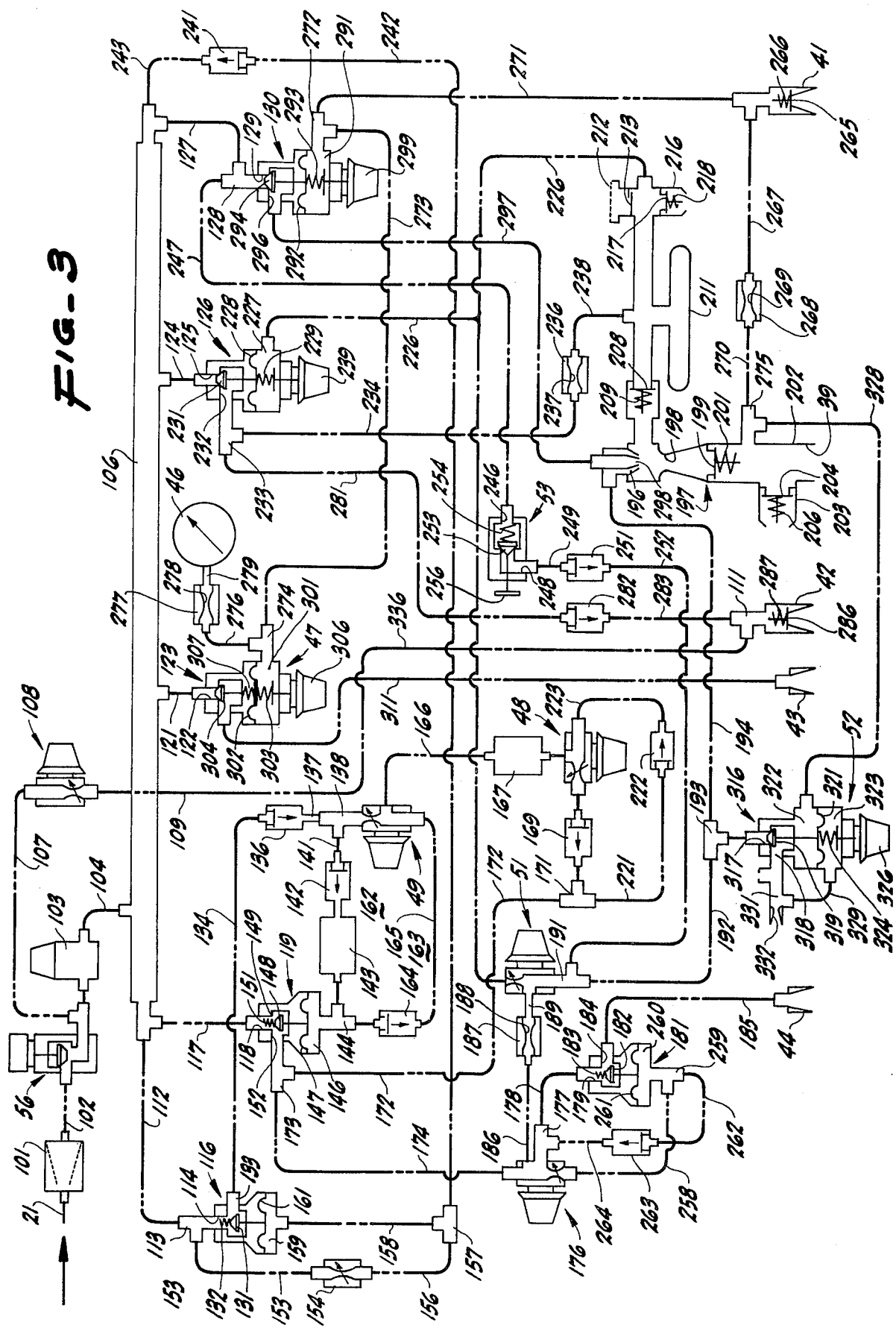
FIG. 3 is a flow diagram partially in schematic form of the ventilator shown in FIGS. 1 and 2.

Operation and use of the ventilator and method of the present invention may not be briefly described in conjunction with the schematic diagram which is shown in FIG. 3. Let it be assumed that a source of gas under a suitable pressure such as 50 psi is supplied to the inlet 21 from the blender 16. This gas, after it enters the case 22, passes through a filter 101 which is connected by tube 102 to the rotary on/off switch or value assembly 56. When the valve assembly 56 is in an "on" position, the gas is supplied to a pressure regulator 103 which regulates pressure down to a suitable value as, for example, 45 psi. Gas from the pressure regulator is supplied by a tube 104 to a source manifold 106. Gas from the on/off switch or valve assembly 56 is also supplied by tube 107 to an auxiliary nebulization control valve assembly 108. The control valve assembly 108 is connected by a tube 109 to a tee 111 mounted in the nebulization service socket 42.

As soon as the source manifold 106 is pressurized by turning on of the on/off control valve assembly 56, source gas is supplied by a tube 112 to a tee 113 mounted in the inlet 114 of a starting autophase cartridge 116. Source gas is also supplied by a tube 117 to the inlet 118 of a master cartridge 119. Source gas is also supplied by a tube 121 to the inlet 122 of an automatic baseline compensator cartridge 123 which is provided with an end expiratory pressure control valve assembly 47. Source gas is also supplied through a tube 124 to the inlet 125 of an entrainment reservoir refill servo assembly 126. Source gas is also supplied through a tube 127 to a tee 128 mounted in an outlet 129 of a demand flow accelerator servo cartridge 130.

As hereinbefore explained, upon operation of the rotary on-off valve assembly 57, source gas is supplied to the inlet 14 of the starting autophase cartridge 116. The starting autophase cartridge 116 is provided with a valve member 131 which is yieldably urged toward a normally open position by a spring 132 to permit gas flow from the inlet 114 through an outlet 133. This source gas is then supplied through a tube 134 through a one-way autophase bypass check valve 136 which is connected by tube 137 to a tee 138 mounted upon the inspiratory time control valve assembly 49. Another leg of the tee 138 is connected by tube 141 to another one-way check valve 142 which is connected to a balance reservoir 143. The balance reservoir 143 is connected to a tee 144 mounted upon the diaphragm side of a master cartridge 119 to supply source gas under pressure to a chamber 146 provided within the cartridge 119 on one side of a diaphragm 147.

The diaphragm 147 is adapted to control the movement of a valve member 148 movable between open and closed positions with respect to a valve seat 149. The valve member 148 is yieldably held in a normally open position by a spring 151. Thus, it can be seen that very shortly after the on-off valve assembly 56 is moved to the open position, the chamber 146 will be pressurized to move the diaphragm 147 to move the valve member 148 into a closed position to prevent source gas 117 from flowing from the inlet to the outlet 152 of the master cartridge 119. As soon as the valve member 148 is moved to the closed position in the master cartridge 119, the ventilator 11 is placed in the expiratory phase because it stops further flow of source gases through the master cartridge 119.

Thus, it can be seen that the starting autophase cartridge 116 ensures that very shortly after the on-off switch or valve assembly 56 is operated or moved to the on position, the ventilator will be switched to the expiratory phase and thereby serves to prevent an inordinately long inspiratory phase and also to prevent the ventilator from staying in the inspiratory phase when there is insufficient pressure to close the master cartridge 119. Operation of the master cartridge 119 causes interruption of the inspiratory phase if the ventilator was in the inspiratory phase. Even if the ventilator was not in the inspiratory phase, the master cartridge will still be operated in the same way to thereby interrupt or prevent the flow of source gas through the master cartridge 119.

As soon as the master cartridge has been cycled to the closed position, it is desirable to lock out the starting autophase cartridge 116. This is accomplished by bleeding source gas from the tee 133 through a tube 153 which is connected to one side of an adjustable needle valve 154 that is provided for calibration of the starting autophase cartridge 116. A tube 156 connects the needle valve assembly 154 to a tee 157. One leg of the tee 157 is connected to a tube 158 to the cartridge 116 and is in communication with a chamber 159 provided in the cartridge 116 on one side of a diaphragm 161. The chamber 159 will be pressurized at a controlled rate as determined by the adjustment of the needle valve assembly 154. When the chamber 159 is pressurized sufficiently, the diaphragm 161 will cause the valve member 131 to be moved to a closed position against the force of the spring 132. This will prevent the flow of source gas from the inlet 114 to the outlet 133 of the starting autophase cartridge 116. This prevents the flow of further source gas into the inspiratory timing circuit 162 for the master cartridge 119 consisting of the balance reservoir 143 and the chamber 146.

Thereafter, the pressurized gas is bled out of the timing circuit by the gas passing through an expiratory bypass circuit 163 which includes a check valve 164 which is connected to the tee 144. The check valve 164 is connected to a tube 165 which is connected to the manifold of the inspiratory time control valve assembly 49 and then to a tube 166 which is connected to an expiratory time accumulator 167 that is connected to the manifold of the expiratory time control valve assembly 48. The gas then passes through the adjustable restricted orifice provided by the expiratory time control valve assembly 48 and thence through a check valve 169 and then through a tee 171 which is connected to a tube 172. The tube 172 is connected to a tee 173 which is connected to the outlet 152 of the master cartridge 119. One leg of the tee 173 is connected by a tube 174 to the manifold of a lock-out time control valve assembly 176. A tee 177 is mounted on the manifold of the control valve assembly 176 and is connected by tube 178 to the inlet 179 of a lock-out cartridge 181. The lock-out cartridge 181 is provided with a valve member 182 which is normally yieldably retained in an open position by spring 183 so that gas flowing in the inlet 179 can flow out the outlet 184. The outlet 184 is connected by tube 185 to the inspiratory power socket 44 which, as hereinbefore described, is connected by the tube 87 to the 500 cc nebulizer 68 and to the exhalation valve assembly 76 which is in an open position during the exhalation phase to permit the gas to flow to ambient. Thus, after a predetermined period of time required for the gas to bleed out of the chamber 146, the spring 151 will cause the valve member 147 of the master cartridge 119 to be moved to an open position to initiate the inspiratory phase.

The master cartridge 119 is of the type described in copending applicaton Ser. No. 593,667, filed July 7, 1975 and now U.S. Pat. No. 4,044,763. As therein explained, the master cartridge 119 operates on a differential pressure in which the closing pressure is significantly greater than the opening pressure as, for example, by ratio of 2:1. As explained in said copending application Ser No. 593,667 filed July 7, 1975, this is due to the fact that as soon as the valve member 147 is moved to an open position, the piston effect created by the source gas is greatly increased because the source gas obtains access to the diaphragm seal which applies a force to cause the valve member 147 to reman in an open position until a significantly greater force than that required for opening the valve is applied to the valve member 147 by means of gas in the chamber 146 to move the diaphragm 147 to cause the valve member 147 to be moved to a closed position. By way of example, the valve member 147 can be moved to a closed position by a pressure of 17 psi and will open when the pressure falls to 8 psi.

In bleeding off the chamber 146 of the master cartridge as hereinbefore described, it should be noted that the bleed-off rate is determined by the adjustment of the expiratory time control valve assembly 48. Thus, the expiratory time can be precisely controlled by the adjustment of the control knob on the expiratory time control valve assembly 48. As soon as the pressure within the chamber 146 has decreased to a certain value as, for example, 8 psi, the valve member 147 will move to the open position to commence the inspiratory phase.

Upon initiation of the respiratory phase, source gas will flow from the source manifold 106 through the line 117 through the inlet 118 of the master cartridge 119 and through the outlet 152 where it will flow in two directions. Source gas will flow through the tube 174 to the lock-out time control assembly 176, through the line 178 and through the normally open lock-out cartridge 181 and through the tube 185 to the inspiratory power socket 44 and to the tube 87 and into the nebulizer 68 and through the line 89 to close the exhalation valve assembly 76. In addition, source gas will be supplied from the manifold 106 to the lock-out time control valve assembly 176 through a tube 186 and through a member 187 having a fixed stabilization orifice 188 therein. The member 187 is connected by a tube 189 to the manifold of the inspiratory flow rate control valve assembly 51 and which has a tee 191 mounted therein. A tube 192 is connected to the tee 191 which is connected to another tee 193. Another tube 194 is connected to the tee 193 and is connected to the outer jets 196 of a master venturi assembly 197. The source gases passing from the jets 196 pass through the venturi 198 and cause opening of a normally closed gate valve 199 which is yieldably held in a normally closed position by a spring 201.

The master venturi assembly is mounted upon a manifold 202 which is secured to the front panel 38 and opens through the breathing tube receptacle 39 provided on the front panel. The manifold 202 is provided with an over-pressure governor 203 which includes a gate valve 204 which is normally yieldably held in a closed position by a spring 206. Thus, it can be seen that source gases are delivered through the manifold 202 through the breathing tube receptacle 39 and then into the large tube 69, the water trap assembly 71, the large tube 72 to the breathing head 73 and through the patient adapter 74 to the airways of the patient.

During the inspiratory phase, additional gases are normally introduced into the breathing circuit by the master venturi 197 as soon as the sub-ambient condition is created by the master venturi by the introduction of gases from the outer jets 196. This sub-ambient condition causes opening of the normally closed entrainment gate valve 208. The gate valve 208 is yieldably held in a normally closed position by a spring 209. Opening of the gate valve 208 permits gases in the entrainment reservoir 211 to be supplied to the master venturi 197. In the event that additional gases are still required in the master venturi 197, ambient air can be entrained through an ambient inlet filter 212. The inlet filter is provided with a normally closed flapper valve 213 which moves to an open position when a sub-ambient condition is created on one side of the valve 213. In the event an over-pressure condition occurs in the entrainment reservoir 211, an overfill relief valve 216 is connected to the entrainment reservoir and includes a gate valve 217 which is normally held in a closed position by yieldable means in the form of a spring 218.

The length of the inspiratory phase is timed by an inspiratory timing circuit which is supplied with gas from the outlet 152 of the master cartridge 119 through the tube 172 and the tee 171 where it flows through a tube 221 through the inspiratory bypass check valve 222 through the tube 223, through the manifold of the expiratory time control valve assembly 48 and then through the expiratory time accumulator 167 through the tube 166 and then through the inspiratory time control valve assembly 49, through the tee 138, the tube 141, the check valve 142, the balance reservoir 142, the tee 144 to the chamber 146 of the master cartridge 119.

The inspiratory phase continues until a sufficient pressure has been built up within the chamber 146 to apply pressure to the diaphragm 146 to move the valve member 148 to a closed position to stop the flow of source gas from the inlet 118 to the outlet 152 and to thereby terminate the inspiratory phase. The balance reservoir 143, as pointed out previously, makes it possible to utilize less expensive needle control valve assemblies as, for example, the one utilized for the inspiratory time control valve assembly 49 while still retaining the desired degree of accuracy.

In the event that gas is introduced into the breathing circuit from the entrainment reservoir 211 to reduce the pressure therein, this reduction in pressure is sensed through a tube 226 which is connected to the chamber 227 on one side of a diaphragm 228 of the entrainment reservoir refill servo valve assembly 126. As soon as the diaphragm 228 is moved towards the chamber 227 because of the decreased pressure within the chamber 227 against the force of a spring 229, a valve member 231 will be moved to an open position to permit source gas to flow from the inlet 122 into an outlet 232 which has a tee 233 mounted therein. The tee 233 is connected by a tube 234 to a member 236 having a restricted orifice 237 therein. The member 236 is connected by a tube 238 to the entrainment reservoir 211. This filling continues until a pressure is sensed in the chamber 227 which is sufficient to cause the diaphragm 228 to move the valve member 231 to a closed position. The force which can be exerted by the spring 229 can be adjusted by adjustment of the knob 239. The orifice 237 serves to limit the rate of flow of gases into the entrainment reservoir 211 so as to not unduly affect the pressure of the source gas being supplied to other parts of the ventilator.

At the termination of the inspiratory phase, the master cartridge 119 interrupts the total source of inspiratory flow. The inspiratory servoing circuit which is comprised of all the components serving the inspiratory service circuit including the master venturi assembly 197 is rapidly depressurized by venting inspiratory gases through the master venturi jets 196 and through the jets in the nebulizer. This causes a reverse flow gradient of gases through the inspiratory timing circuit.

Timing of the expiratory phase commences as soon as the inspiratory gas pressure is reversed at the metered outlet provided by the expiratory time control valve assembly 48. Because of the approximately 10 psi differential between the opening and closing of the master cartridge 119 as hereinbefore explained, the effective pressure rise and fall between inspiration and expiration is 10 psi.

As hereinbefore explained, the length of the expiratory phase is determined by the period of time required to bleed down the gas which is present in the chamber 146 and in the balance reservoir 143 which must pass through the expiratory bypass check valve 164 through line 165, line 166, through the expiratory time control valve 48 which is provided with an adjustable orifice to control the rate of flow, then through the check valve 169, line 172, line 174, line 178 through the lock-out cartridge 181, through the line 185 and thence to the 500 cc nebulizer 68 and to the exhalation valve assembly 76. Another bleed-off path is provided through the line 186, through the stabilization orifice 188, the line 192, line 194, through the jets 196 and through the master venturi 198 and thence to ambient through the exhalation valve assembly 76.

As soon as the pressure in the chamber 146 has been bled down sufficiently as, for example to 8 psi, as pointed out above, the master cartridge 119 will open to terminate the expiratory phase and to initiate a new inspiratory phase.

The timing circuitry hereinbefore described provides the logic for repetitive time cycling of the ventilator through both the inspiratory and the expiratory phases of the ventilator. The two check valves 142 and 169 are provided to isolate the inspiratory and expiratory timing functions. As can be seen, the inspiratory isolation check valve 142 is located at the metering outlet of the inspiratory time control valve assembly 49 and the expiratory isolation check valve 169 is located at the metering outlet of the expiratory time control valve assembly 48. Both isolation check valves prevent reverse flow of gases through their respective timing valve assemblies.

As hereinbefore pointed out, with a timed cyclic system and with a normally open master cartridge 119, the initial inspiratory phase can be longer than the program interval for the inspiratory phase because of the flow time required to fill the timing circuit. This could deliver a tidal volume to the patient well in excess of that programmed when the timing circuit is first pressurized. The autophase cartridge 116 prevents the first breath tidal voume delivered to the patient from being larger than that programmed and serves to instantly charge the timing circuit by sequencing a starting expiratory phase.

The autophase timing circuit is charged by source gas flow through the autophase calibration metering orifice 154. This adjustable metering orifice is calibrated to meter flow sufficient to deliver a servoing pressure against the diaphragm 161 of the starting autophase cartridge 116 in a relatively short period of time as, for example, 1 second.

The autophase timing circuit is instantly reset when the source manifold 106 is depressurized. Depressurization of the source manifold causes a pressure drop on the outlet side of the autophase reset check valve 241 which is connected to the tee 157 by a tube 242. The other side of the autophase reset check valve 241 is connected to the source manifold 106 by tube 243. Thus, it can be seen that as soon as the source manifold 106 is depressurized, the check valve 241 is permitted to open and will dump the gas in the autophase timing circuit into the source manifold including the chamber 159 to permit the starting autophase cartridge 116 to be automatically returned to its open position.

The inspiratory phase can be manually initiated by use of the manual inspiration pushbutton assembly 253. Inlet 246 is connected by tube 247 to the tee 128 mounted on the demand flow accelerator servo assembly 130 and is thereby connected to source pressure from the manifold 106 through the tube 127. The outlet 248 is connected by a tube 249 to one end of a manual bypass check valve assembly 251. The other end of the check valve 251 is connected by a tube 252 to the tee 191 mounted on the inspiratory flow rate valve assembly 51. The manual inspiration pushbutton assembly 53 is provided with a valve member 253 which is normally yieldably held in a closed position to prevent the passage of gas from the inlet 246 to the outlet 248 by a spring 254. A finger operated pushbutton 256 is provided for manually operating the valve member 253 so that it can be depressed against the force of the spring 254 to permit source gas to flow from the source manifold through the tube 127, tube 247, through the manual inspiration pushbutton valve assembly 53, through the tube 249 through the manual bypass check valve assembly 251, tube 252, through the tee 191 and then through the tube 192, tee 193, tube 194, to the outer jets 196 of the master venturi assembly 197. Thus, it can be seen that manually opening the manual inspiration pushbutton valve assembly 53 bypasses the master cartridge 119 and directs source gas into the inspiratory circuit. This causes a normal program inspiratory flow into the breathing circuit of the patient with simultaneous programming of the timing circuit into the expiratory phase. Therefore, as long as the manual pushbutton valve assembly 53 is held in an open position, the ventilator will be held in the inspiratory phase or until a lockout occurs as initiated by the lockout cartridge 181 after a predetermined period period of time as, for example, 5 seconds.

During the time that the pushbutton 256 is being depressed, the timing circuit is being loaded so that when the finger releases the pushbutton 256, the respirator or ventilator will go into the expiratory phase immediately or very soon thereafter depending upon the amount of time required for the timing circuit to time out. As explained previously, this is determined by the amount of time required for gas to flow from the source manifold 106 to the line 117, through the open master cartridge 119, through the tube 127, tee 171, tube 221, inspiratory bypass check valve 222, to the line 223, the reservoir 167, line 166, through the inspiratory time control valve assembly 49, through the tee 138, through the check valve 142, the balance reservoir 143, and into the chamber 146 to create a sufficient pressure in the chamber 146 to move the valve member 148 to a closed position to terminate the inspiratory phase.

As hereinbefore explained, the entrainment reservoir refill servo valve assembly 126 automatically keeps the venturi entrainment reservoir 211 filled for the inspiratory entrainment of respiratory gases by the master venturi assembly 197. The entrainment reservoir is serviced by the gated inlet filter 212 for ambient entrainment of gases should physiological demand exceed the mechanical refill rate for the reservoir. The entrainment reservoir 211 is protected aganst overfilling by the gated ambient overfill relief valve 216.

The venturi entrainment system provided by the master venturi assembly provides a pneumatic clutching action for pulmonary conformance while maintaining a constant selectable mixture of respiratory gases.

An accessory spring-loaded directional check valve 208 is provided between the outlet of the entrainment reservoir 211 and the entrainment port of the master venturi assembly 197. By establishing a relief pressure of a suitable value as, for example, 6 cm of $H_2O$ on the accessory entrainment gate valve assembly 208 and another higher predetermined pressure as, for example, 8 cm of $H_2O$ on the overfill relief valve 217, the entrainment refill and entrainment circuit can be maintained independent of the master venturi gate 199.

The provision of this accessory entrainment gate 208 provides several advantages. The master venturi is proximally gated to provide more constant tidal volumes under conditions of major compliance shift in the patient. IMV nebulization is increased when the entrainment refill circuit is employed to provide intermittent inspiratory nebulization. This is created by the more acute opening and closing of the entrainment refill servo valve assembly 126 with higher peak delivery pressures during initial inspiration when entrainment demands are the highest.

During the inspiratory phase, gas is bled at a controlled rate as determined by the adjustment of the lock-out time control valve assembly 176 and supplies gas through a tube 258 connected to a tee 259 mounted on the lock-out cartridge 181. The tee 259 is in communication with a chamber 260 provided in the cartridge 181 on one side of the diaphragm 261 which is utilized for moving the valve member 182 to a closed position against the force of the spring 183. Thus, it can be seen after a predetermined period of time as determined by the adjustment of the lock-out time control valve assembly 176 as, for example, in 5 seconds, the lock-out cartridge 181 will be activated to prevent further flow of gases through the inspiratory power socket 44 to permit the exhalation valve to open and to terminate the inspiratory phase. The tee 259 is connected to a tube 262 which is connected to a lock-out reset check valve assembly 263 which is connected by a tube 264 to the tee 177. The lock-out reset check valve assembly 263 serves to dump the chamber 260 into the depressurized service circuit during each repetitive mechanical expiratory phase to guarantee constant time accumulation during each new inspiratory phase prior to a lock-out occurring.

A sensing circuit is provided in the ventilator which monitors proximal airway pressures. This sensing circuit includes the airway pressure monitoring socket 41 which, as hereinbefore described, is connected by tube 83 to the breathing head assembly 73. The socket 41 is provided with a gate valve 265 which is normally held in a closed position by spring 266. This socket 41 is connected by tube 267 to a member 268 having a fixed internal sensing orifice 269 provided therein. The other end of the member 268 is connected by tube 270 to a tee 275 which is mounted upon the master venturi in the manifold 202. When a bayonet (not shown) carried by the tube 83 is positioned in the airway pressure monitoring socket 41, the gate valve 265 is opened. Opening of the circuit overwhelms the minute pathway provided by the internal sensing orifice 269.

The pressure which is being sensed and supplied to the socket 41 is connected by tube 271 to a tee 272 mounted upon the demand flow accelerator servo valve assembly 130. The tee 272 is connected by tube 273 to a tee 274 mounted on the end expiratory pressure control valve assembly 47. The tee 274 is connected by tube 276 to one end of a member 277 having a fixed restricted orifice 278 provided therein. The other end of the member 277 is connected by tube 279 to the manometer 46. Thus, it can be seen that a breathing pressure rise or drop is communicated to the airway pressure monitor or manometer 46.

This same proximal airway pressure is transmitted to the sensing port of the demand flow accelerator servo valve assembly 130 as well as to the sensing port of the automatic baseline compensator cartridge 123.

It should be understood that when the bayonet for the tube 43 is withdrawn from the airway pressure monitoring socket 41 that the monitoring returns to that provided by the internal sensing orifice 266. This orifice 266 dampens the pressure change between the distal end of the master venturi 197 and the proximal airway of the patient.

A secondary source of nebulization for the humidification of inspiratory gases for the patient is provided by the entrainment reservoir refill servo valve assembly 126 as hereinafter described. Generally, maximum entrainment by the master venturi 197 would be expected during the first half of the inspiratory phase with a gradual tapering back until back pressures against the distal venturi gate in the master venturi to cause minimal entrainment of additional gases from the entrainment reservoir 211 toward the end of active inspiration. This would cause a maximum pressure drop in the reservoir during early inspiration with a gradual pressure rise occurring until complete refill of the reservoir has occurred. The outlet of the entraiment servo 126 is connected to the nebulization service socket 42 through a tube 281, through a check valve 282, thence through a tube 283, the tee 111 to the nebulization service socket 42. This provides a secondary source of nebulization and is activated when the bayonet (not shown) carried by the tube 84 is inserted into the nebulization service socket 42 to open a check valve 286 which is normally held in a closed position by spring 287. The nebulizer pressure rise orifice 237 restricts flow into the entrainment reservoir and increases the pressure of the source gas entering the nebulizer servo socket and thereby increases nebulizer output.

If, during the expiratory phase in normal timed cycle or cyclic ventilation, the patient attempts to breathe spontaneously, this attempt of the patient to breathe will create a sub-ambient condition. This will be sensed immediately through the airway pressure monitoring socket 41 and is delivered to a chamber 291 of the demand flow accelerator servo valve assembly 130 and causes a diaphragm 292 to move against the yieldable force provided by a spring 293 to move a valve member 294 to an open position to permit source gas to flow from the source manifold 106 through the tube 127, the tee 128, to the outlet 296. The gas is supplied from the outlet 296 through a tube 297 to the center jet 298 of the master venturi. This jet of gas from the center jet 298 of the master venturi will cause opening of the gate valve 199 and will cause entrainment of gases from the entrainment reservoir 211 in the manner hereinbefore described in connection with the delivery of gases through the outer jets 196 of the master venturi to cause a flow of gas through the breathing tube outlet 39 and into the main breathing tube 69 to the breathing head 73 and into the lungs of the patient.

Thus, it can be seen that the ventilator can provide flow at respiratory rates upon demand of the patient. The amount of effort required by the patient to generate flow can be determined by adjustment of the knob 299 provided on the demand flow accelerator servo valve assembly 130 which increases or decreases the pressure applied by the spring 293 on the diaphragm 292. By way of example, the valve assembly 138 can be adjusted so that it will move the valve member 294 to an open position under any pressure which is less than a positive 1 cm of water.

As soon as the patient begins to exhale, as hereinbefore described, positive pressure will be created in the airway pressure monitoring socket 41 to create such a pressure in the chamber 293 to move the valve member 294 in the demand flow accelerator servo valve assembly 130 to a closed position to terminate flow of source gas from the valve assembly 130.

Let it be assumed that it is desired to utilize intermittent mandatory ventilation, hereinafter IMV, in connection with the patient using the ventilator. During the time that the patient is breathing spontaneously, this can be readily accomplished by adjustment of the expiratory time control valve assembly 48. In one extreme position of the control valve assembly 48, the flow of gas through the valve assembly 58 could be cut off completely in which event the ventilator would be completely under the control of the breathing pattern of the patient and thus would require the patient to breathe spontaneously. Then, if the expiratory time control valve assembly 48 is gradually opened, this will gradually decrease the expiratory time. If the patient has the capability of breathing spontaneously, the demand flow accelerator servo valve assembly 130 will be actuated to deliver a flow of source gas during the timed expiratory phase. The greater the length of time provided by the expiratory time control valve assembly 48, the more control the patient will have to take with respect to initiation of inspiratory phases of the ventilator. Thus, a manadated inspiratory phase will only occur at the end of the time provided by the expiratory time control valve assembly 48. At this time, a mandated inspiratory phase will be initiated to delivery inspiratory source gases to the patient under the control of the ventilator. As the length of time provided by the expiratory time control 48 is decreased, fewer and fewer mandatory breaths will be provided by the ventilator. By decreasing the rate of flow through the valve assembly 48, the expiratory times are increased to such an extent that the mandatory ventilation is essentially blocked out and the ventilator is under the spontaneous control of the patient. By increasing the rate of flow, the number of mandated breaths can be increased to such a rate that the patient will be essentially unable to take a spontaneous breath.

The demand flow accelerator servo valve assembly 130 is capable of delivering IMV inspiratory gases without requiring a sub-ambient servoing pressure drop. By way of example, the demand flow accelerator servo cartridge 130 is calibrated by adjustment of the knob 299 to deliver inspiratory gases when pressures in the sensing and breathing circuits fall below approximately 2 cm of $H_2O$. This allows almost effortless physiological access to inspiratory gases upon demand by the patient during IMV procedures. By delivering gases upon physiological inspiratory demand under a 2 cm $H_2O$ positive pressure drop, resistances to flow within the entire breathing circuit are overcome.

During the spontaneous expiratory phase of IMV, pressures in the breathing circuit remain slightly above 2 cm of $H_2O$ because of the slight resistance to expiratory flow offered by the expiratory side of the breathing circuit as well as the 2-3 cm of $H_2O$ closing force mandated by the spring holding the gate valve closed provided in the exhalation valve assembly 76. Interruption of the IMV gases during the expiratory phase conserves respiratory gases and reduces the operating cost of IMV procedures.

With the ventilator it is possible to provide a constant positive airway pressure against which the patient must exhale. This feature is provided by the automatic baseline compensator cartridge 123 which carries the end expiratory pressure control valve assembly 47. As pointed out previously, the airway pressure monitoring socket 41 is in communication with a tube 273 which is connected to the tee 274 mounted upon the automatic baseline compensator cartridge 123. The tee 274 is in communication with a chamber 301 provided in the cartridge 123 which is disposed on one side of a diaphragm 302. Adjustable spring means which includes a spring 303 engages one side of the diaphragm 302 and yieldably urges the diaphragm 302 and the valve member 304 actuated thereby in a direction so that the valve member 304 is moved towards a closed position. The pressure exerted by the spring 303 on the diaphragm 302 is controlled by adjustment of the knob 306. Another spring 307 is provided in the cartridge 203 and applies a yieldable force to the diaphragm 302 to move it in such a direction that the valve member 304 is moved towards an open position. The size of the springs 303 and 307 is such that the force exerted by the spring 307 is greater than that exerted by the spring 303 so that the valve member 304 is in a normally open position.

As the knob 306 is adjusted, the spring force on the diaphragm 302 is increased or decreased depending upon the direction of rotation of the knob 306. In addition, to the force of the spring 307 tending to move the diaphragm to open the valve member 304, there is the piston effect created by the source gas upon the piston 304 tending to move the piston to an open position. By way of example, the knob 306 can be adjusted to provide 10 cm of constant positive airway pressure (CPAP) so that the cumulative spring tension in combination with 10 cm of $H_2O$ pressure in the chamber 101 by urging the diaphragm 302 holds the valve member 304 in a closed position. Whenever the pressure in the chamber 301 drops below 10 cm of $H_2O$ in the patient breathing circuit, the valve member 304 will begin to open and will supply source gas from the source manifold 106 through the tube 119, through the automatic baseline compensator cartridge 123, through a tube 311 which is connected to the baseline deviation power socket 43. The source gas under pressure is supplied through the tube 36 to the nozzle 77 of the venturi member 75 of the breathing head 73 where the gas under pressure is supplied through the venturi-like passageway 78 and into the patient adapter 74 to develop a positive pressure at the patient's airway so that the patient must exhale against this positive pressure.

If the patient takes a breath, this will be sensed by the fitting 81 in the hole 79 of the venturi member 75 and this reduced pressure will be supplied through the tube 86 to the socket 44 and thence to the chamber 301 of the automatic baseline compensator cartridge 123 which will cause movement of the diaphragm 320 to move the valve 304 to a further open position to increase the flow of gas to the baseline deviation power socket 43 and to thereby attempt to maintain a constant positive airway pressure at the breathing head against which the patient must exhale, Thus, it can be seen that for any selected CPAP, flow into the breathing circuit is precisely controlled to maintain that preselected value. As CPAP pressures in the breathing circuit rise to the selected CPAP value, the automatic baseline compensator cartridge 123 gradually reduces flow into the breathing circut to maintain a predetermined post end expiratory pressure in a static or resting position. As CPAP pressures in the breathing circuit rise above the CPAP, baseline flow into the breathing circuit is retarded until zero flow from the automatic baseline deviation compensator cartridge 123 occurs.

Thus, it can be seen that the baseline deviation compensator cartridge 123 serves to automatically servo inflow during post expiratory end procedures to maintain an exact positive end expiratory pressure against which the patient must exhale. During the spontaneous phase of the IMV procedure as hereinbefore described, the baseline deviation compensator cartridge 123 plays another major role in maintaining a CPAP during spontaneous inspiratory physiological demand. It prevents a massive downward baseline shift during normal spontaneous inspiratory demand. As CPAP in the breathing circuit moves downwardly from the baseline selected on the compensator cartridge 123, the secondary flow inspiratory gas is delivered at the proximal airway through the CPAP venturi jet hereinbefore described. Supplemental flow into the breathing circuit maintains an existing static CPAP during inspiratory demand increases as downward deviation from CPAP occurs.

By way of example, one automatic baseline deviation compensator cartridge provided in a ventilator was programmed to provide a maximum static CPAP of 40 cm of $H_2O$. The higher the CPAP selected, the more rapid the rate of breathing circuit inflow CPAP falls below the programmed values.

In the event a source gas interruption should occur or in the event of blocking inspiratory flow, the spontaneously breathing patient would be able to entrain ambient air through the ambient inlet filter 212. By utilization of CPAP techniques, it is possible to increase the functional residual capacity of the lungs of the patient. By utilizing such a technique, the ventilator holds the lungs partially inflated. This technique is utilized on patients having acute pulmonary disease with a decreased functional residual capacity. Such a patient breathes out too much air from his lungs and has insufficient air in his lungs to provide adequate mixing.

Automatic inspiratory compensation is provided by the automatic inspiratory compliance compensator cartridge 316 in conjunction with the inspiratory flow acceleration pressure control valve assembly 52. The cartridge 316 is provided with an inlet 317 and an outlet 318. A valve member 319 is provided in the cartridge 316 and is normally yieldably held in a closed position to prevent the flow of gas from the inlet 317 to the outlet 318. A diaphragm 321 is provide in the cartridge and has chambers or compartments 322 and 323 formed on opposite sides of the same within the cartridge. A spring 324 yieldably urges the diaphragm 321 in a direction to move the valve member 319 to a closed position. The force applied by the spring 324 can be adjusted by roation of a knob 326. The chamber 322 is connected by tube 328 to the tee 268 mounted on the manifold 202 in which the master venturi 197 is mounted. The other compartment 323 is connected by tube 329 to a fitting 331 mounted in the outlet 318 of the automatic inspiratory compliance compensator cartridge. The fitting 331 is provided with an orifice 332 which is open to ambient or the atmosphere.

The control knob 326 is adjusted so that until a greater than a predetermined pressure is reached within the chamber 322, the valve member 319 will remain in a closed position. For example, the knob 326 can be adjusted so that the valve member 319 will not open unless a pressure greater than 20 cm of $H_2O$ is reached in the chamber 322. Thus, when a pressure greater than the predetermined pressure is reached in the breathing circuit, this condition will be sensed in the tube 328 and supplied to the chamber 322 to apply pressure to the back side of the diaphragm 321 to move the valve member 319 towards an open position to permit gas to flow from the tube 192 during the expiratory phase and to pass through the cartridge 316 and to be bled to the atmosphere through the orifice 332. Thus, the more the pressure in the breathing circuit rises above the predetermined pressure, the valve 319 will be opened still further to bleed additional gas from the tube 192 supplying gas to the outer jets 196 of the master venturi. Thus, it can be seen that as the pressure rises in a breathing circuit above a predetermined pressure, the increase in pressure tapered off because there will be less and less flow coming in through the outer jets 196 because of the bleed-off of some of the gases through the orifice 332.

Thus, at the start of inspiration or upon a mandated breath, gas will be flowing through the inspiratory drive power line 192 to the outer jets 196 of the master venturi assembly 197. In addition, gas will be supplied to the inspiratory power socket 44 to close the exhalation valve assembly. The pressure build-up within the breathing circuit will be transmitted back to the airway pressure monitoring socket 41 to close off flow through the demand flow accelerator servo cartridge 130 and also to close off the automatic baseline compensator cartridge 123. This same pressure being sensed is also supplied through the line 328 to the automatic inspiratory compliance compensator cartridge 316. As explained previously, by adjusting knob 36, it is possible to relieve the pressure within the breathing circuit after the pressure has reachhed a predetermined value so that the pressure increase tapers off.

The flow of bleed-off gases through the venturi-like passage provided in the orifice 332 creates a sub-ambient condition which is supplied by the tube 329 to the chamber 323 to cause further opening of the valve member 319 to cause a further reduction in pressure in the breathing circuit. This action will continue until the inspiratory phase is terminated.

The demand flow accelerator servo carttridge 130 with the position of the proximal airway venturi sensing port 79 provides a means for the demand flow accelerator servo cartridge 130 to self-servo. This self-servoing occurs because upon the initial patient demand, this condition is sensed at the port 79 and is supplied to the demand flow accelerator servo cartridge 130 and also to the automatic baseline compensator cartridge 123. As flow through the tube 86 from the cartridge 123 increases there will be increased flow through the venturi-like passageway 78 to create an additional pressure drop at the sensing port 79 which information will be supplied to the cartridges 123 and 130 to further augment the flows therethrough. The sensitivity of the sensing port 79 can be adjusted by changing the position of the port with respect to the passageway 78. As it is moved closer to the narrower portion of the passageway 78 it becomes more sensitive. Thus, it can be seen that this mechanical combination shares in the creating of spontaneous physiological inspiration.

In situations where very low tidal volumes are required, it has been found that it is desirable to provide additional gas pressure for nebulization under such circumstances. This has been provided in the present ventilator by the separate auxiliary neubilization control valve assembly 108 connected to the output from the on-off rotary switch 56 by the tube 107. The output from the control valve assembly 108 is connected by a tube 336 to the tee 111 which is mounted in the nebulization service socket 42 to provide additional gas for nebulization.

The ventilator hereinbefore described is provided with many safety features. The over-pressure governor 203 limits the maximum pressure which can be exerted against the physiological airway of a patient while still permitting a prolonged apneustic pressure.

Closing off the flow of gases to the inspiratory power socket 44 permits the exhalation valve to open and permits the patient to freely exhale. The ventilator will stay locked out until the timing circuit sequences into the expiratory phase at which time the chamber 260 of the lockout cartridge will be dumped into the master venturi and out the exhalation valve. The next inspiratory phase will commence after expiration of the expiratory phase or under the demand of the patient if the patient is breathing spontaneously.

By using distal and proximal gates 199 and 209 on the master venturi assembly 197, a means is provided to allow venturi clutching during the early part of the inspiratory phase up to that point at which the venturi completely stalls. Without a proximal gate when the venturi stalls, gas leaving the jet of the venturi essentially reverses flow and is exiled through the venturi entrainment port. By using a proximal gate, the gas issuing from the venturi jet after the full stall has occurred is blocked by the proximal gate and is forced from the venturi through the distal gate into the patient breathing circuit. The advantage is that tidal volumes are maintained at higher levels when gross pulmonary compliance of the patient decreases. Thus, minute volumes are maintained at more constant levels with moderate changes in pulmonary resistance.

As hereinbefore explained, the inspiratory flow deceleration which is accomplished by the automatic inspiratory compliance compensator cartridge 316 is highly advantageous in controlling the distribution of alveolar gases in the patient with a stiff fibrotic lung or with a generalized obstructive pulmonary disease. Under these circumstances, it is desirable to slow the flow rate down as pressures rise providing more uniform distribution of pulmonary gases.

However, it has been found that there is another group of patients which have essentially normal lungs but who use their expiratory musculature to splint the lung and thereby inhibit the delivery of tidal volumes. Such patients are patients with neurologic and renal dysfunctions, among others. Among such patients it has been found that during the inspiratory phase of a timed cycle ventilator using a clutching master venturi, the pressure rise due to decreased gross pulmonary compliance is very rapid. As the pressure rise passes the stalling position of the master venturi, there is the loss of the associated gases which would be entrained into the master venturi 197 and for this reason the actual tidal volume can be much less than the volume which would be expected with a normal lung. An even worse situation occurs when a patient keeps changing his gross pulmonary compliance when he changes from higher to lower levels because of neurogenic disturbances.

In the schematic diagram shown in FIG. 4, there is shown an embodiment of the ventilator incorporating the present invention which is provided with means for maintaining a more stable tidal volume during periods of changing gross pulmonary compliance of the patient. As can be seen, the schematic diagram shown in FIG. 4 is very similar to the one shown in FIG. 3 with the principal changes being associated with the automatic inspiratory compliance compensator 351. It is provided with an inlet 352 which is in communication with an outlet 353. The communication with inlet 352 and the outlet 353 can be interrupted by a valve member 354 which is provided with a valve stem 356 that is connected to a diaphragm 357. A spring 358 is provided for yieldably urging the diaphragm 357 and the valve member 354 carried thereby in a direction to move the valve member 354 to a closed position to interrupt the flow of gases from the inlet 352 to the outlet 353. The force exerted by the spring 358 on the diaphragm 357 can be adjusted by use of the adjustment knob 359.

The cartridge is provided with a chamber 361 which is on the sensing side of the diaphragm 357 opposite the spring 358. The chamber 361 is connected by a tube 362 to the airway pressure monitoring socket 41 which is connected to the patient breathing circuit in the manner hereinbefore described in conjunction with FIG. 3. The other side of the diaphragm 357 is open to the atmosphere through the outlet 363. Source gas is supplied to inlet 352 of the cartridge 351 through a tube 364 which is connected to the outlet of the on-off switch 56. When the valve member 354 is in an open position, the source gas is supplied from the inlet 352 through the outlet 353 to a tube 366 and thence through a one-way check valve 367 which is connected by tube 368 to the center jet 298 of the master venturi assembly 197. The outer jets 196 are connected directly to the inspiratory flow rate control valve assembly 51 by line 369.

Operation of the ventilator utilizing the automatic inspiratory compliance compensator 351 may now be briefly described as follows. Let it be assumed that the operation of the ventilator is the same as hereinbefore described with the exception that the cartridge 351 has taken the place of the cartridge 316. When it is found that the pulmonary compliance of a patient decreases, it is possible to adjust the knob 359 to select a point in the pressure rise in the patient breathing circuit which is monitored through the airway pressure monitoring socket 41 and the information supplied to the chamber 361 of the cartridge 351. When the pressure rise is sufficient, the diaphragm 357 will be depressed against the force of the spring 358 and the valve member 354 will be moved toward the open position to permit source gas to flow from the line 364 through the inlet 352 and thence through the outlet 353, through the one-way check valve 367 and through the center jet 298 of the master venturi assembly 197 to provide an additional flow through the master venturi assembly which when added to the gas already being supplied to the master venturi makes up for gas which is no longer being entrained through the accessory entrainment gate after the master venturi has reached a stall point. Thus, gas will continue to be supplied to the patient through the cartridge 351 until the inspiratory phase is terminated in the manner hereinbefore described in conjunction with FIG. 3. As soon as the inspiratory phase is terminated, the pressure will drop in the airway pressure monitoring socket 41 to permit the valve member 354 to again move to a closed position to prevent the flow of additional source gas from the line or tube 364 into the line 368.

The adjustable spring-loading provided in the cartridge 351 which is utilized for holding the valve 354 in a closed position is capable of maintaining the valve member in the closed position with sensing pressures as high as or above the relief pressures of the breathing circuit which by way of example can be on the order of 110 cm of $H_2O$. In such a position, inspiratory flow acceleration would not occuur; however, when the closing spring-loading against the diaphragm is reduced, the pressure rise against the sensing side of the diaphragm will force the valve member 354 of the cartridge 351 to an open position at a given pressure and admit source gas into the breathing circuit through the master venturi assembly as hereinbefore described.

If the adjustable knob 359 is set so that a pressure rise of 40 cm of $H_2O$ is required in the pressure monitoring socket 41 before the valve member 354 is moved to an open position, this typically could correspond to the adjusted velocity through the master venturi assembly where a stall would occur. By having the valve member 354 open at this pressure, the drop-off of inspiratory flow associated with the stall when entrainment ceased would allow additional inspiratory flow acceleration to occur at that point which would deliver the same amount of gases as that being entrained or more into the breathing circuit through the master venturi assembly 197.

Thus, it can be seen that a major advantage of the automatic inspiratory compliance compensator is that it inhibits or even prevents a drop in tidal volume in which occurs when the entrainment or clutching action of the master venturi assembly begins to slip. Thus, it can be seen with the automatic inspiratory compliance compensator cartridge 351, it is possible to obtain a more constant tidal volume as pulmonary resistances increase.

A ventilator of the type shown in FIG. 4, in addition to being useful for human patients would also be of great advantage in ventilating some larger animals or in the case where there is inspiratory splinting of the lungs during the inspiratory phase because of disturbances in the neurological respiratory control. A great advantage of the ventilator shown in FIG. 4 is that it is possible to utilize pneumatic clutching during the early stages of the inspiratory phase up to a point where there is no longer any entrainment because of the stall effect in the venturi, at which point the flow would be augmented from the automatic inspiratory compliance compensator cartridge 351 to maintain the same flow into the breathing circuit.

In this way, it can be seen that with a timed cycle ventilator it is possible to approximate the tidal volume delivered to the patient as accurately as with a piston or bellows-type mechanical volume delivery.

It should be appreciated that, if desired, a needle valve assembly could be placed in the outlet of the cartridge 351 to control the rate at which flow acceleration will enter the breathing circuit.

The ventilator hereinbefore described can be classified as a pressure limited controller with flow and pressure variables under obligatory time cycling wih intermittent mandatory ventilation. In addition, there is provided automatically programmed demand constant positive airway pressure as well as automatic compliance compensation.

As also can be seen from the construction herein disclosed, the ventilator is of modular design making it relatively simple to manufacture and repair. It has sufficient functions that it can be utilized as a primary intensive care intermittent mandatory ventilation ventilator for all age groups. Adjustable peak pressure limiting is provided.

What is claimed is:

1. In a ventilator having an inhalation phase and an exhalation phase in its operative cycle for use with a source of gas under pressure, an inlet adapted to be connected to the source of gas under pressure, master control valve means having an inlet and an outlet and a valve member movable between open and closed positions for controlling the flow of gas from the inlet to the outlet, means connecting the inlet of the control valve means to the inlet of the ventilator, said valve member being in an open position during the inspiratory phase and in a closed position during the expiratory phase of the ventilator, said master control valve means including a diaphragm which upon movement causes movement of the valve member, said control valve means having a chamber formed on one side of the diaphragm, a breathing head assembly, said breathing head assembly including an exhalation valve assembly, means for supplying gas from the outlet of the control valve means to the breathing head assembly, timing means connected between the outlet of the control valve means and said chamber for timing the introduction of gases into said chamber during the inspiratory phase and the bleeding of gases from said chamber during the expiratory phase to thereby control the movement of the valve member to initiate the inspiratory and expiratory phases of the ventilator, means for sensing the pressure of the gases in the breathing head assembly and baseline compensation means connected to the inlet of the ventilator and responsive to the sensed pressure in the breathing head assembly for supplying gas to the exhalation valve assembly so that the patient must exhale against a substantially constant positive pressure, said baseline compensation means including an inlet and an outlet with the inlet being connected to the inlet of the ventilator and the outlet being connected to the exhalation valve assembly, a valve member movable between open and closed positions for controlling the flow of gas from the inlet to the outlet of the baseline compensation means, said baseline compensation means including a diaphragm and means forming a chamber on one side of the diaphragm whereby upon movement of the diaphragm the valve member is moved between said open and closed positions, means connecting the chamber of the baseline compensation means to means for sensing the pressure of the gases in the breathing circuit, yieldable spring means for yieldably urging the diaphragm of the baseline compensation means in a direction to cause movement of said valve member and means for causing adjustment of said spring means.

2. A ventilator as in claim 1 together with demand flow accelerator means connected to the inlet and means connected to the means for sensing the pressure of the gases in the breathing head assembly for supplying gases to the breathing head assembly when the pressure in the breathing head assembly is below a predetermined pressure.

3. A ventilator as in claim 2 wherein said demand flow accelerator means includes an inlet coupled to the inlet of the ventilator, and an outlet coupled to the breathing head assembly and a valve member movable between open and closed positions for controlling the flow of gas between the inlet and the outlet of the demand flow accelerator means, said demand flow accelerator means including a diaphragm and means forming a chamber on one side of the diaphragm whereby when gas is supplied to the chamber, the diaphragm is moved to cause movement of the valve member, said demand flow accelerator means including spring means for applying yieldable pressure to the diaphragm of the demand flow accelerator means and means for adjusting the force supplied by the spring means to the diaphragm of the demand flow accelerator means and means for connecting the chamber of the demand flow accelerator means to the means for sensing the pressure in the breathing head assembly.

4. A ventilator as in claim 1 together with inspiratory compliance compensating means having an inlet connected to the breathing head assembly, and an outlet open to the atmosphere and a valve member movable between open and closed positions for controlling the flow of gas between the inlet and the outlet, said inspiratory compliance compensation means including means responsive to the means for sensing pressure of the gases in the breathing head assembly for controlling the movement of the valve member to permit some of the gases being supplied to the breathing head assembly to be bled out to the atmosphere when the pressure in the breathing head assembly exceeds a predetermined pressure.

5. A ventilator as in claim 4 wherein said inspiratory compliance compensation means includes a diaphragm and means forming a chamber on one side of the diaphragm whereby upon changes in pressure in the chamber, forces are applied to the diaphragm to cause the diaphragm to cause movement of the valve member of the inspiratory compliance compensation means whereby as the pressure being sensed increases beyond a predetermined pressure, gases to be bled from the gases being supplied to the breathing head assembly and vented to the atmosphere.

6. A ventilator as in claim 5 wherein said inspiratory compliance compensation means includes means forming a chamber on the opposite side of the diaphragm and wherein said means forming an outlet for the gases from the inspiratory compliance compensating means includes a venturi for creating a negative pressure and means for supplying the negative pressure to the chamber on the other side of the diaphragm.

7. A ventilator as in claim 6 together with spring means for yieldably applying a force to the diaphragm of the inspiratory compliance compensation means and means for adjusting the force applied by the spring means.

8. A ventilator as in claim 1 together with means connected to the timing means for causing lock-out of an inspiratory phase in the event the inspiratory phase exceeds a predetermined time.

9. A ventilator as in claim 8 together with means for supplying gas from outlet of the master control valve means to the exhalation valve assembly to maintain the exhalation valve assembly in a closed position during the exhalation phase and wherein said lock-out means includes means for interrupting the flow of gases to said exhalation valve means so that said exhalation valve means can move to an open position after expiration of said predetermined period of time.

10. A ventilator as in claim 9 wherein said lock-out means includes an inlet for receiving gas from the master control valve means, an outlet connected to the exhalation valve means and a valve member movable between open and closed positions for controlling the flow of gases from the inlet to the outlet of the lock-out means, said lock-out means including a diaphragm, means forming a chamber on one side of the diaphragm and timing means connected between the outlet of the control valve means and the chamber for supplying gases to the chamber of the lock-out means at a controlled rate so that the valve member of the lock-out means will be moved to a closed position within a predetermined time during which the expiratory phase should have commenced.

11. A ventilator as in claim 10 together with means for dumping the chamber in the lock-out means during the expiratory phase of the ventilator.

12. A ventilator as in claim 1 wherein said timing means includes inspiratory time control valve means and expiratory time control valve means for establishing a ratio between inspiratory timme and the expiratory time.

13. A ventilator as in claim 12 wherein said inspiratory and expiratory time control valve means have outlets together with check valve means at the outlets of said inspiratory and expiratory control valve means for ensuring that the inspiratory time and expiratory time are completely independent of each other.

14. A ventilator as in claim 13 together with balance reservoir means connected into the timing circuit to reduce the criticality of the inspiratory time control valve means and the expiratory time control valve means.

15. In a ventilator having an inhalation phase and an exhalation phase in its operative cycle for use with a source of gas under pressure, an inlet adapted to be connected to the source of gas under pressure, master control valve means having an inlet and an outlet and a valve member movable between open and closed positions for controlling the flow of gas from the inlet to the outlet of the master control a valve means, means connecting the inlet of the control valve means to the inlet of the ventilator, said valve member being in an open position during the inspiratory phase and in a closed position during the expiratory phase of the ventilator, said master control valve means including a diaphragm and means forming a chamber on one side of the diaphragm whereby when gases are supplied to the chamber, the diaphragm can be moved to cause movement of the valve member, a breathing head assembly, said breathing head assembly including an exhalation valve assembly, means for supplying gases from the outlet of the control valve mean to the breathing head assembly, pneumatic timing circuit means connected between the outlet of the control valve means and said chamber for timing the introduction of gases into the chamber and bleeding of gases from the chamber to thereby control movement of the valve member to initiate the inspiratory and expiratory phases of the ventilator, said pneumatic timing means including an inspiratory time control valve assembly and an expiratory time control valve assembly, each having an inlet and an outlet, means including a one-way inspiratory bypass check valve means interconnecting the inlet and outlet of the expiratory time control valve assembly, said expiratory time control valve assembly and an expiratory time accumulator coupling the outlet of the master control valve means to the inlet of the inspiratory time control valve assembly for bypassing the expiratory time control valve assembly, means including a one-way expiratory bypass check valve means interconnecting the inlet and outlet of the inspiratory time control valve assembly, said inspiratory time control valve assembly and said expiratory time accumulator coupling the chamber of the master control valve means to the inlet of the expiratory time control valve assembly for bypassing the inspiratory time control valve assembly, means including one-way isolation check valve means and a balance reservoir coupling the outlet of the inspiratory time control valve assembly to said chamber of said master control valve means and disposed within the interconnection of said one-way expiratory bypass check valve means and said inspiratory time control valve assembly and means including one-way isolation check valve means coupling the outlet of expiratory time control valve assembly to the outlet of said master control valve means and disposed within the interconnection of said one-way inspiratory bypass check valve means and said inlet and outlet of said expiratory time control valve assembly.

16. A ventilator as in claim 15 together with reservoir means connected into the timing circuits to reduce the criticality of control by the inspiratory time control valve means and the expiratory time control valve means.

17. A ventilator as in claim 16 together with lock-out means for locking out the inspiratory phase after a predetermined period of time.

18. A ventilator as in claim 15 together with inspiratory flow rate means for controlling the rate of flow of gases to the breathing circuit.

19. A ventilator as in claim 15 together with demand flow accelerator means connected to the inlet means for sensing the pressure in the breathing head assembly for controlling the operation of the demand flow accelerator whereby when the pressure in the breathing head assembly drops below a predetermined value, gases are supplied to the breathing head assembly by the demand flow accelerator means.

20. A ventilator as in claim 15 together with means for providing baseline compensation means connected to the inlet and having means connected to the means for sensing the pressure in the breathing circuit for causing gas under pressure to be supplied to the breathing head assembly so that the patient must exhale against a constant positive airway pressure.

21. A ventilator as in claim 15 together with means connected to the breathing head assembly and having an outlet and means connected to the means for sensing the pressure in the breathing head for causing gas to be bled from the gas being supplied to the breathing head and to vent them to the atmosphere.

22. A ventilator as in claim 15 together with means connected to the inlet of the ventilation for causing the initiation of an expiratory phase prior to the initiation of an inspiratory phase.

23. A ventilator as in claim 22 wherein said means for causing initiation of the expiratory phase prior to the initiation of the inspiratory phase includes starting means having an inlet connected to the inlet of the ventilator and an outlet connected to the timing circuit and normally open valve means movable between open and closed positions for controlling the flow of gas from the inlet to the outlet of the starting means, said starting means including a diaphragm and means forming a chamber on one side of the diaphragm whereby when gas is supplied to the chamber, the valve member is caused to move to the closed position and means for supplying gas from the inlet of the ventilator to the chamber of the starting means to cause movement of the valve member to prevent further flow of gases from the inlet to the outlet of the starting means when a predetermined pressure is reached in the chamber.

24. In a ventilator having an inhalation phase and an exhalation phase in its operative cycle for use with a source of gas under pressure, an inlet adapted to be connected to the source of gas under pressure, master control valve means having an inlet and an outlet and a valve member movable between open and closed positions for controlling the flow of gas from the inlet to the outlet, means connecting the inlet of the control valve means to the inlet of the ventilator, said valve member being in an open position during the inspiratory phase and in a closed position during the expiratory phase of the ventilator, said master control means including a diaphragm which upon movement causes movement of the valve member, said control valve means having a chamber formed on one side of the diaphragm, a breathing head assembly, said breathing head assembly including an exhalation valve assembly, means including a master venturi assembly for supplying gas from the outlet of the control valve means to the breathing head assembly, timing means connected between the outlet of the control valve means and said chamber for timing the introduction of gases into and the bleeding of gases from said chamber to thereby control the movement of the valve member to initiate the inspiratory and expiratory phases of the ventilator and inspiratory compliance compensating means for controlling of the flow of gases to the master venturi assembly during the inspiratory phase, said inspiratory compliance compensating means including an inlet and an outlet, a valve member movable between open and closed positions for interrupting the flow of gases from the inlet to the outlet, a diaphragm connected to the valve member and adjustable spring means applying force to the diaphragm to yieldably retain the valve member in a closed position, said inlet of the inspiratory compliance compensating means being coupled to the master venturi assembly and the outlet being open to the atmosphere and means coupling the inspiratory compliance compensating means to the breathing head assembly whereby when a predetermined pressure is reached, the valve member is moved to an open position to permit gases to be bled from the master venturi assembly to the atmosphere.

25. In a ventilator having an inhalation phase and an exhalation phase in its operative cycle for use with a source of gas under pressure, an inlet adapted to be connected to the source of gas under pressure, control valve means movable between open and closed position for controlling the flow of gas from the inlet to the outlet, a breathing head assembly, said breathing head assembly including a member having a venturi-like passageway therein, a patient adapter in communication with said venturi-like passageway in said member, a sensing port mounted in said member in the vicinity of said venturi-like passageway, nozzle means carried by said member for introducing a jet of gases into said venturi-like passageway, an exhalation valve assembly in communication with said member, means for supplying gas from the outlet of the control valve means to said member whereby the same can be delivered to the patient adapter, demand flow accelerator means having an inlet connected to the inlet of the ventilator and having an outlet in communication with said member, baseline compensation means having an inlet connected to the inlet of the ventilator and having an outlet coupled to the nozzle for delivering a jet of gases to the venturi-like passageway of the member and means coupled to the sensing port for delivering pressure information to the demand flow accelerator means whereby when the patient takes a breath, the reduction in pressure will be sensed by the demand flow acceleration means and by the baseline compensation means to cause continued augmentation of the flow through the demand flow accelerator means and the automatic baseline compensation means.

26. In a ventilator having an inhalation phase and an exhalation phase in its operative cycle for use with a source of gas under pressure, an inlet adapted to be connected to a source of gas under pressure, master control valve means having an inlet and an outlet and a valve member movable between open and closed positions for controlling the flow of gas from the inlet to the outlet, means connecting the inlet of the control valve means to the inlet of the ventilator, said valve member being in an open position during the inspiratory phase and in a closed position during the expiratory phase of the ventilator, said master control means including a diaphragm which upon movement causes movement of the valve member, said control valve means having a chamber formed on one side of the diaphragm, a breathing head assembly, said breathing head assembly including an exhalation valve assembly, means including a master venturi assembly for supplying gas from the outlet of the control valve means to the breathing head assembly, timing means connected between the outlet of the control valve means and said chamber for timing the introduction of gases into and the bleeding of gases from said chamber to thereby control the movement of the valve member to initiate the inspiratory and expiratory phases of the ventilator and inspiratory compliance compensating means for controlling the flow of gases to the master venturi assembly during the inspiratory phase, said inspiratory compliance compensating means including an inlet and an outlet and valve means movable between open and closed positions for controlling the flow of gases between the inlet and the outlet, a diaphragm which upon movement causes movement of the valve member, adjustable spring means for yieldably applying a force to the diaphragm to maintain the valve member in a normally closed position, means coupling the inlet of the inspiratory compliance compensating means to the source of gas under of gas under pressure, means coupling the outlet to the master venturi assembly and means coupling the diaphragm to the breathing assembly whereby when a predetermined pressure is reached in the breathing head assembly, the diaphragm will be moved against the force of the spring means to move the valve member to an open position to permit source gas to flow from the inlet to the outlet and into the master venturi assembly to augment the flow of gases through the master venturi assembly during the inspiratory phase.

27. In a ventilator having an inhalation phase and an exhalation phase in its operative cycle for use with a source of gas under pressure, an inlet adapted to be connected to the source of gas under pressure, master control valve means having an inlet and an outlet and a valve member movable between open and closed positions for controlling the flow of gas from the inlet to the outlet, means connecting the inlet of the control valve means to the inlet of the ventilator, said valve member being in an open position during the inspiratory phase and in a closed position during the expiratory phase of the ventilator, said master control valve means including a diaphragm which upon movement causes movement of the valve member, said control valve means having a chamber formed on one side of the diaphragm, a breathing head assembly, said breathing head assembly including an exhalation valve assembly, means for supplying gas from the outlet of the control valve means to the breathing head assembly, timing means connected between the outlet of the control valve means and said chamber for timing the introduction of gases into and the bleeding of gases from said chamber to thereby control the movement of the valve member to initiate the inspiratory and expiratory phases of the ventilator and inspiratory compliance compensating means having an inlet connected to the breathing head assembly and an outlet open to the atmosphere, said inspiratory compliance compensating means including a valve member movable between open and closed positions for controlling the flow of gas between the inlet and the outlet of the inspiratory compliance compensating means, a diaphragm coupled to the valve member, means forming a chamber on one side of the diaphragm, means coupling the chamber of the inspiratory compliance compensation means to the breathing head assembly whereby when the pressure being sensed in the breathing head assembly increases beyond a predetermined pressure, the pressure in the chamber of the inspiratory compliance compensation means will move the diaphragm to cause the valve member to move towards an open position whereby gases will be bled from the breathing head assembly and vented to the atmosphere, means forming a chamber on the opposite side of the diaphragm on the inspiratory compliance compensation means and venturi means coupled to the output of the inspiratory compliance compensation means to create a negative pressure for supplying the negative pressure to the chamber on the opposite side of the diaphragm.

28. A ventilator as in claim 27 together with spring means for yieldably applying a force to the diaphragm of the inspiratory compliance compensation means to bias the valve member towards a normally closed position and means for adjusting the force applied by the spring means of the inspiratory compliance compensation means.

29. In a ventilator having an inhalation phase and an exhalation phase in its operative cycle for use with a source of gas under pressure, an inlet adapted to be connected to the source of gas under pressure, master control valve means having an inlet and an outlet and a valve member movable between open and closed positions for controlling the flow of gas from the inlet to the outlet, means connecting the inlet of the control valve means to the inlet of the ventilator, said valve member being in an open position during the inspiratory phase and in a closed position during the expiratory phase of the ventilator, said master control valve means including a diaphragm which upon movement causes movement of the valve member, said control valve means having a chamber formed on one side of the diaphragm, a breathing head assembly, said breathing head assembly including an exhalation valve assembly, means for supplying gas from the outlet of the control valve means to the breathing head assembly, timing means connected between the outlet of the control valve means and said chamber for timing the introduction of gases into and bleeding of gases from said chamber to thereby control the movement of the valve member to initiate the inspiratory and expiratory phases of the ventilator, means for supplying gas from the outlet of the master control valve means to the exhalation valve assembly to maintain an exhalation valve assembly in a closed position during the exhalation phase and lockout means connected to the timing means for causing lockout of the inspiratory phase in the event the inspiratory phase exceeds a predetermined time, said lockout means including an inlet for receiving gas from the master control valve means, an outlet connected to the exhalation valve means and a valve member movable between open and closed positions for controlling the flow of gases from the inlet to the outlet of the lockout means, a diaphragm, means forming a chamber on one side of the diaphragm and means for supplying gas to the chamber of the lockout means at a controlled rate so that the valve member of the lockout means will be moved to a closed position within a predetermined time to interrupt flow of gases to the exhalation valve means so that the exhalation valve means can move to an open position within a predetermined time during which the inspiratory phase should have terminated and the expiratory phase should have commenced.

30. A ventilator as in claim 29 together with means for dumping the chamber in the lockout means during the expiratory phase of the ventilator.

31. A ventilator as in claim 29 together with check valve means at the outlet of said inspiratory and expiratory control valve means for insuring that the inspiratory time and the expiratory time are completely independent of each other.

32. A ventilator as in claim 31 together with balance reservoir means connected into the timing circuit to reduce criticality of the inspiratory time control valve means and the expiratory time control valve means.

33. In a ventilator having an inhalation phase and an exhalation phase in its operative cycle for use with a source of gas under pressure, an inlet adapted to be connected to the source of gas under pressure, master control valve means having an inlet and an outlet and a valve member movable between open and closed positions for controlling the flow of gas from the inlet to the outlet of the master control valve means, means connecting the inlet of the control valve means to the inlet of the ventilator, said valve member being in an open position during the inspiratory phase and in a closed position during the expiratory phase of the ventilator, said master control valve means including a diaphragm and means forming a chamber on one side of the diaphragm whereby when gases are supplied to the chamber, the diaphragm can be moved to cause movement of the valve member, a breathing head assembly, said breathing head assembly including an exhalation valve assembly, means for supplying gas from the outlet of the control valve means to the breathing head assembly, pneumatic timing means having an inlet connected to the outlet of the control valve means and having an outlet connected to said chamber for timing the introduction of gases into the chamber and bleeding of gases from the chamber to thereby control the movement of the valve member to initiate the inspiratory and expiratory phases of the ventilator and means connected to the inlet of the ventilator for causing initiation of the inspiratory phase prior to the initiation of the expiratory phase, said means for causing initiation of the expiratory phase prior to the initiation of the inspiratory phase including starting means having an inlet connected to the inlet of the ventilator and having an outlet connected to the inlet of the timing means, normally open valve means movable between open and closed positions for controlling the flow of gas from the inlet to the outlet of the starting means, a diaphragm, means forming a chamber on the one side of the diaphragm, means for supplying gas from the inlet to the ventilator to the chamber of the starting means to cause movement of the valve member to the closed position to prevent further flow of gases from the inlet to the outlet of the starting means when a predetermined pressure is reached in the chamber.

* * * * *